United States Patent
Schaefer et al.

(10) Patent No.: US 11,542,457 B2
(45) Date of Patent: Jan. 3, 2023

(54) HYDROLYTICALLY LABILE HETEROCYCLES OF ODORIFEROUS KETONES OR ODORIFEROUS ALDEHYDES

(71) Applicant: Henkel AG & Co. KGaA, Duesseldorf (DE)

(72) Inventors: Sascha Wilhelm Schaefer, Mettmann (DE); Benjamin Berntsson, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 206 days.

(21) Appl. No.: 16/765,181

(22) PCT Filed: Oct. 16, 2018

(86) PCT No.: PCT/EP2018/078157
§ 371 (c)(1),
(2) Date: May 19, 2020

(87) PCT Pub. No.: WO2019/101444
PCT Pub. Date: May 31, 2019

(65) Prior Publication Data
US 2020/0283697 A1 Sep. 10, 2020

(30) Foreign Application Priority Data
Nov. 24, 2017 (DE) .................. 10 2017 127 776.5

(51) Int. Cl.
| | | |
|---|---|---|
| C11B 9/00 | (2006.01) |
| A61K 8/49 | (2006.01) |
| A61L 9/01 | (2006.01) |
| A61Q 5/06 | (2006.01) |
| A61Q 15/00 | (2006.01) |
| A61Q 19/10 | (2006.01) |
| C07D 233/58 | (2006.01) |
| C07D 233/60 | (2006.01) |
| C11D 3/28 | (2006.01) |
| C11D 3/50 | (2006.01) |
| C07D 211/36 | (2006.01) |
| C07D 211/40 | (2006.01) |
| C07D 211/54 | (2006.01) |
| C07D 213/60 | (2006.01) |
| C07D 213/62 | (2006.01) |

(52) U.S. Cl.
CPC .......... *C11B 9/0092* (2013.01); *A61K 8/4946* (2013.01); *A61L 9/01* (2013.01); *A61Q 5/06* (2013.01); *A61Q 15/00* (2013.01); *A61Q 19/10* (2013.01); *C07D 211/36* (2013.01); *C07D 211/40* (2013.01); *C07D 211/54* (2013.01); *C07D 233/58* (2013.01); *C07D 233/60* (2013.01); *C11D 3/28* (2013.01); *C11D 3/50* (2013.01); *C07D 213/60* (2013.01); *C07D 213/62* (2013.01)

(58) Field of Classification Search
CPC ... C07D 211/36; C07D 211/40; C07D 211/54; C07D 233/58; C07D 233/60; C07D 213/60; C07D 213/62; A61L 9/01
See application file for complete search history.

(56) References Cited

U.S. PATENT DOCUMENTS

| 10,941,156 B2* | 3/2021 | Schaefer ............... C11D 3/50 |
| 11,104,688 B2* | 8/2021 | Haetzelt ............... C11B 9/0096 |
| 2002/0022039 A1* | 2/2002 | Hofmann ............. C11B 9/0069 426/538 |
| 2003/0158079 A1 | 8/2003 | Dykstra et al. |
| 2004/0072704 A1 | 4/2004 | Gerke et al. |
| 2014/0030397 A1 | 1/2014 | Kropf et al. |
| 2017/0349858 A1 | 12/2017 | Kropf et al. |
| 2020/0102272 A1* | 4/2020 | Schaefer ............. C07D 207/08 |
| 2020/0331935 A1* | 10/2020 | Schaefer ................. A61L 9/01 |

FOREIGN PATENT DOCUMENTS

| DE | 2546192 | * | 4/1976 | |
| DE | 3039056 A1 | | 5/1982 | |
| DE | 102011006314 A1 | | 10/2012 | |
| DE | 102013226098 A1 | * | 6/2015 | ........... C11B 9/0003 |
| DE | 102013226098 A1 | | 6/2015 | |
| EP | 1716159 B1 | | 7/2011 | |

(Continued)

OTHER PUBLICATIONS

Barluenga; Chem. Eur. J. 2004, 10, 494-507. doi: 10.1002/chem. 200305406 (Year: 2004).*

(Continued)

*Primary Examiner* — Daniel R Carcanague
(74) *Attorney, Agent, or Firm* — Viering Jentschura & Partner mbB

(57) ABSTRACT

Heterocycles having odoriferous ketone or odoriferous aldehyde groups may be suitable in compositions comprising washing agents, cleaning agents, cosmetic agents, air care agents, insect repellents, or combinations thereof where the heterocycles release the ketones and aldehydes during hydrolysis. The heterocycle(s) may have the formula:

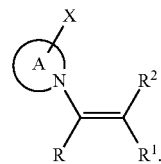

12 Claims, No Drawings

(56) References Cited

FOREIGN PATENT DOCUMENTS

| | | | |
|---|---|---|---|
| GB | 849541 | A | 9/1960 |
| GB | 2319527 | A | 5/1998 |
| JP | 49040223 | * | 10/1974 |
| WO | 9631486 | A1 | 10/1996 |
| WO | 0168037 | A2 | 9/2001 |
| WO | 2016091815 | A1 | 6/2016 |
| WO | 2016096539 | A1 | 6/2016 |

OTHER PUBLICATIONS

Bigdelia; Journal of Chemical Research 2005, 800-801. doi:10.3184/030823405775146942 (Year: 2005).*

Liao; J. Org. Chem. 2009, 74, 16, 6371-6373, with Supporting Information, 44 pages, doi: 10.1021/jo901105r (Year: 2009).*

Tsuchimoto; Eur. J. Org. Chem. 2008, 4035-4040, and supporting information pp. 1-116. DOI: 10.1002/ejoc.200800353 (Year: 2008).*

Hermann; Chem. Unserer Zeit, 2015, 49, 36-47; with English Translation. http://dx.doi.org/10.1002/ciuz.201400677 (Year: 2015).*

International search report from parallel PCT Patent Application PCT/EP2018/078157 dated Jan. 7, 2019, 12 pages (for reference purposes only).

Huang et al., "Rhodium(III)-Catalyzed Direct Selective C(5)-H Oxidative Annulations of 2-Substituted Imidazoles and Alkynes by Double C-H Activation", Organic Letters, 2013, pp. 1878-1881, vol. 15, No. 8.

Kalman et al., "Inhibition of Cellular Thymidylate Synthesis By Cytotoxic Propenal Derivatives of Pyrimidine Bases and Deoxynucleosides", Biochemical Pharmacology, 1991, pp. 431-437, vol. 42, No. 2.

Jokic et al., "Stereocontrolled Conversion of 1-(3-Hydroxyprop-1-enyl)uracil isomers into Polyfunctional 3,9-Propano-and 3,9(9,3)-Propeno-aza-9H-xanthines", Journal of the Chemical Society Perkin Transactions 1, 1990, pp. 2225-2232.

Johnson et al., "Synthesis and Biological Activity of a New Class of Cytotoxic Agents: N-(3-Oxoprop-1-enyl)-Substituted Pyrimidines and Purines", Journal of Medical Chemistry, 1984, pp. 954-958, vol. 27, No. 8.

* cited by examiner

HYDROLYTICALLY LABILE HETEROCYCLES OF ODORIFEROUS KETONES OR ODORIFEROUS ALDEHYDES

CROSS-REFERENCE TO RELATED APPLICATIONS

The present application is a national stage entry according to 35 U.S.C. § 371 of PCT application No.: PCT/EP2018/078157 filed on Oct. 16, 2018; which claims priority to German Patent Application Serial No.: 10 2017 127 776.5, which was filed on Nov. 24, 2017; which are incorporated herein by reference in their entirety and for all purposes.

TECHNICAL FIELD

The present description relates to heterocycles, in particular enamines, which contain groups of odoriferous ketones or odoriferous aldehydes and are suitable, for example, for fragrancing laundry, since they release the ketones or aldehydes during hydrolysis.

BACKGROUND

In the field of washing and cleaning agents, the controlled release of fragrances in order to provide the product, as well as the washing and cleaning solution and the articles treated with these agents, with an intensive and long-lasting fragrance is known in the prior art. In addition to the methods of applying fragrances to carrier materials and coating the fragranced carriers, or encapsulating fragrances or incorporating them into compounds, there is the option of chemically bonding the fragrances to carrier media, the chemical bond being slowly broken and the fragrance being released.

It is known in the prior art to bind fragrant alcohols to non-volatile siloxanes, from which they are slowly released by hydrolysis. For example, WO 01/068037 A2 and GB 2319527 A describe mixtures of oligomeric silicic acid esters which contain groups of fragrant alcohols and are suitable, for example, for fragrancing washing and cleaning agents. Further polymeric siloxanes which are used as pro-fragrances for alcohols, carbonyls, unsaturated ketones and aldehydes are described, for example, in EP 1716159 B1 and WO 2016/091815 A1.

Silyl enol ethers of fragrance aldehydes and ketones are described, for example, in DE 10 2013 226 098 A1. The problem addressed was to provide alternative precursors of odorants which allow sustained release of the odorants and use low molecular weight anchor groups, which optionally also impart adhesion to the surfaces to be fragranced, such as textile surfaces. Furthermore, precursors should be provided which have a higher efficiency in providing the fragrance.

SUMMARY

The inventors have now surprisingly found that such compounds can be prepared by utilizing the keto-enol tautomerism of odoriferous ketones and aldehydes, the cleavage of which then brings about the aldo or keto form again during or after the application via back-tautomerization. Although keto-enol tautomerism is generally well known, the equilibrium of ketones and aldehydes which have not been additionally functionalized is usually very much on the side of the carbonyl compound. However, the inventors have now found that by capturing the enol form and converting it to a storage-stable heterocyclic compound, the enol can be removed from equilibrium so that eventually the complete ketone or aldehyde is converted to the corresponding heterocycle form.

In a first aspect, heterocycles may include the formula

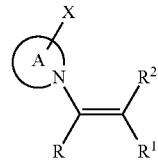

wherein
R, $R^1$ and $R^2$ are independently selected from H, straight-chain or branched, saturated or unsaturated, substituted or unsubstituted hydrocarbon groups having 1 to 20 carbon and optionally up to 6 heteroatoms, such as linear or branched alkyl, alkenyl or alkynyl having up to 20, such as up to 12 carbon atoms, substituted or unsubstituted, linear or branched heteroalkyl, heteroalkenyl or heteroalkynyl having up to 20, such as up to 12 carbon atoms, and 1 to 6, such as 1 to 4 heteroatoms selected from O, S and N, substituted or unsubstituted aryl having up to 20, such as up to 12 carbon atoms, substituted or unsubstituted heteroaryl having up to 20, such as up to 12 carbon atoms, and 1 to 6, such as 1 to 4 heteroatoms selected from O, S and N, cycloalkyl or cycloalkenyl having up to 20, such as up to 12 carbon atoms, and heterocycloalkyl or heterocycloalkenyl having up to 20, such as up to 12 carbon atoms, and 1 to 6, such as 1 to 4 heteroatoms selected from O, S and N, or R and $R^1$ or R and $R^2$ can combine with each other to form a cyclic group, which is selected from substituted or unsubstituted aryl having up to 20, such as up to 12 carbon atoms, substituted or unsubstituted heteroaryl having up to 20, such as up to 12 carbon atoms, and 1 to 6, such as 1 to 4 heteroatoms selected from O, S and N, substituted or unsubstituted cycloalkyl or cycloalkenyl having up to 20, such as up to 12 carbon atoms, and substituted or unsubstituted heterocycloalkyl or heterocycloalkenyl having up to 20, such as up to 12 carbon atoms, and 1 to 6, such as 1 to 4 heteroatoms selected from O, S and N, with the proviso that at least one of R, $R^1$ and $R^2$ is not H and the group —O—CR=$CR^1R^2$ is derived from an odoriferous ketone or odoriferous aldehyde of formula R—C(O)—$CHR^1R^2$; and A is a cyclic, such as aromatic, hydrocarbon group containing at least one nitrogen atom in the cycle and bonds via this nitrogen atom to the rest of the molecule, wherein in A further carbon atoms may be replaced by N, O, or S, and at least one hydrogen atom of A may be substituted with a substituent X, wherein X is selected from —F, —Cl, —Br, —$NO_2$, —OH, =O, —$CH_3$, —$CH_2CH_3$.

The preparation of the compounds mentioned can be carried out by means of the synthesis routes described in the examples. In the starting materials, the hydrogen atom is acidic with respect to the carbonyl group. The heterocycle used carries an acidic hydrogen atom on a nitrogen. Ideally, 4 equivalents of the heterocycle are reacted in the first step with 1 equivalent of thionyl chloride to give the corresponding thiourea derivative. The reaction with 1 further equivalent of thionyl chloride after filtration now yields the corresponding heterocycle-substituted thionic acid chloride. Subsequently, the addition of the ketone or aldehydes can take place. Care should be taken that less than 1 equivalent is added in drops so as to avoid a self-aldol reaction. Ideally, the temperature is monitored during the addition. This should not exceed 30° C.

In a further aspect, the use of heterocycles as described herein as a fragrance in liquid or solid washing and cleaning agents or in cosmetic agents, in particular those for skin or hair treatment, optionally together with other fragrances, in insect repellents or air care agents may prolong the fragrance effect of other fragrances.

Yet another aspect is directed to agents containing the heterocycles described herein, in particular washing or cleaning agents, cosmetic agents, air care agents or insect repellents.

Lastly, a method is disclosed for long-lasting fragrancing of surfaces, in which a compound as described herein is applied to the surface to be fragranced, for example (textile) laundry, and said surface is subsequently exposed to conditions which lead to the fragrance being released.

DETAILED DESCRIPTION

"At least one," as used herein, refers to 1 or more, for example 2, 3, 4, 5, 6, 7, 8, 9 or more. In connection with components of the compound described herein, this information does not refer to the absolute amount of molecules, but to the type of the component. "At least one compound of formula X" therefore means, for example, one or more different compounds of formula X, i.e. one or more different types of compounds of formula X. Together with amounts, the amounts refer to the total amount of the corresponding designated type of ingredient, such as already defined above.

Unless otherwise indicated, all amounts indicated in connection with the agents described herein refer to wt. %, in each case based on the total weight of the agent. Moreover, amounts that relate to at least one component always relate to the total amount of this type of component contained in the agent, unless explicitly indicated otherwise. This means that specified amounts of this type, for example in connection with "at least one anionic surfactant," refer to the total amount of fragrance contained in the agent.

In the context herein, the term "odoriferous ketones" is understood to mean fragrances which have a keto group which exhibits keto-enol tautomerism, regardless of how the molecule is further structured. By analogy, "odoriferous aldehydes" is understood to mean herein fragrances having an aldehyde group which exhibits keto-enol tautomerism, regardless of how the molecule is further structured. As a prerequisite for the phenomenon of keto-enol tautomerism, it is necessary that the corresponding ketones and aldehydes can be deprotonated in alpha or alpha beta unsaturated molecules in gamma position, i.e. at least one H atom is bound at the alpha or gamma C atom. Such deprotonatable ketones and aldehydes are therefore the odoriferous ketones or aldehydes which form the heterocycles. The terms "odorant" and "fragrance" are used interchangeably herein and refer in particular to substances that have a fragrance that is perceived to be pleasant by humans. In various embodiments, fragrances are those substances that are sufficiently volatile to be perceived as odorous by humans by binding to the olfactory receptor, and which have an odor that is perceived as pleasant. The fragrances or odorants are in particular those which are suitable for use in cosmetic compositions and cleaning agent or washing agent compositions. Generally, the fragrances or odorants are liquid at ambient temperatures.

In various embodiments, the odoriferous aldehyde may be selected from Adoxal (2,6,10-trimethyl-9-undecenal), Cymal (3-(4-isopropylphenyl)-2-methylpropanal), Florhydral (3-(3-isopropylphenyl)butanal), helional (3-(3,4-methylenedioxyphenyl)-2-methylpropanal), hydroxycitronellal, lauraldehyde, Lyral (3- and 4-(4-hydroxy-4-methylpentyl)-3-cyclohexene-1-carboxaldehyde), methylnonylacetaldehyde, Lilial (3-(4-tert-butylphenyl)-2-methylpropanal), phenylacetaldehyde, undecylenealdehyde, 2,6,10-trimethyl-9-undecenal, 3-dodecene-1-al, melonal (2,6-dimethyl-5-heptenal), 2,4-dimethyl-3-cyclohexene-1-carboxaldehyde (Triplal), 3-(4-tert-butylphenyl)-propanal, 2-methyl-3-(para-methoxyphenyl)propanal, 2-methyl-4-(2,6,6-trimethyl-2(1)-cyclohexen-1-yl)butanal, cis/trans-3,7-dimethyl-2,6-octadien-1-al, 3,7-dimethyl-6-octen-1-al, [(3,7-dimethyl-6-octenyl)oxy]acetaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methane-1H-indenecarboxaldehyde, alpha-methyl-3,4-(methylenedioxy)-hydrocinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxy-hexahydro-4,7-methanindane-1 or 2-carboxaldehyde, 3,7-dimethyloctan-1-al, 1-undecanal, 10-undecene-1-al, 1-methyl-3-(4 methylpentyl)-3-cyclohexenecarboxaldehyde, 7-hydroxy-3,7-dimethyl-octanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, 3,5,6-trimethyl-3-cyclohexene carboxaldehyde, 3,7-dimethyl-2-methylene-6-octenal, phenoxyacetaldehyde, 5,9-dimethyl-4,8-decadienal, peonyaldehyde (6,10-dimethyl-3-oxa-5,9-undecadiene-1-al), hexahydro-4,7-methanindane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 3,5,5-trimethylhexanal, hexahydro-8,8-dimethyl-2-naphthaldehyde, 3-propylbicyclo[2.2.1]-hept-5-ene-2-carbaldehyde, 9-decenal, 3-methyl-5-phenyl-1-pentanal, methylnonylacetaldehyde, hexanal, trans-2-hexenal and mixtures thereof.

Non-limiting aldehydes include, without limitation, Lilial, Helional, cyclamen aldehyde, Triplal, Melonal, methylundecanal, undecanal, nonanal and octanal.

Suitable ketones include, but are not limited to Nectaryl (2-(2-[4-methyl-3-cyclohexen-1-yl]propyl)cyclopentanone), 2-undecanon (methylnonylketone), methyl-beta-naphthylketone, musk indanone (1,2,3,5,6,7-hexahydro-1,1,2,3,3-pentamethyl-4H-inden-4-one), tonalide (6-acetyl-1,1,2,4,4,7-hexamethyltetraline), alpha-damascone, beta-damascone, delta-damascone, iso-damascone, damascenone, methyldihydrojasmonate, menthone, carvone, camphor, Koavone (3,4,5,6,6-pentamethylhept-3-en-2-one), fenchone, alpha-ionone, beta-ionone, gamma-methyl-ionone, Fleuramone (2-heptylcyclopentanon), dihydrojasmone, cis-jasmone, 1-(1,2,3,4,5,6,7,8-octahydro-2,3,8,8-tetramethyl-2-naphthalenyl)-ethan-1-one and isomers thereof, methylcedrenylketone, acetophenone, methylacetophenone, para-methoxyacetophenone, methyl-betanaphtylketone, benzyl acetone, para-hydroxyphenylbutanon, celery ketone (3-methyl-5-propyl-2-cyclohexenone), 6-isopropyldeca-hydro-2-naphtone, dimethyloctenone, Frescomenthe (2-butan-2-ylcyclohexan-1-one), 4-(1-ethoxyvinyl)-3,3,5,5-tetramethylcyclohexanone, methylheptenone, 2-(2-(4-Methyl-3-cyclohexen-1-yl)-propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascol, dulcinyl (4-(1,3-benzodioxol-5-yl)butan-2-one), hexalone (1-(2,6,6-trimethyl-2-cyclohexen-1-yl)-1,6-heptadien-3-one), isocyclemone E (2-acetonaphthone-1,2,3,4,5,6,7,8-octahydro-2,3,8,8-tetramethyl), methylcyclocitrone (1-(3,5,6-trimethyl-1-cyclohex-3-enyl)ethanone), methyllavenderketone (3-hydroxymethylnonan-2-one), orivone (4-tert-amylcyclohexanone), 4-tert-butyl cyclohexanone, Delphone (2-pentyl cyclopentanone), Muscone (CAS 541-91-3), Neobutenone (1-(5,5-dimethyl-1-cyclo-hexenyl)pent-4-en-1-one), Plicatone (CAS 41724-19-0), Veloutone (2,2,5-trimethyl-5-pentylcyclopentan-1-one), 2,4,4,7-tetramethyl-oct-6-en-3-one, Tetramerane (6,10-dimethylundecen-2-one) and mixtures thereof.

Moreover, all customary odoriferous aldehydes and/or odoriferous ketones can, in principle, be used as odoriferous aldehydes and/or odoriferous ketones, which are in particular used for bringing about a smell which is pleasant to humans and are capable of keto-enol tautomerism. Such odoriferous aldehydes and/or odoriferous ketones are known to a person skilled in the art and are also described in the patent literature, for example in US 2003/0158079 A1, paragraphs [0154] and [0155]. For further suitable odorants, reference should be made to: Steffen Arctander, Aroma Chemicals Volume 1 and Volume 2 (published in 1960 and 1969, reissue 2000; ISBN: 0-931710-37-5 and 0-931710-38-3).

In various embodiments, the heterocycles are those resulting from odoriferous ketones, in particular those mentioned above. In various embodiments, the odoriferous ketones are those in which neither the alpha carbon atom nor the beta carbon atom (each relative to the oxygen atom) is a component of a cyclic group.

In various embodiments, R is a straight-chain or branched, saturated or unsaturated, substituted or unsubstituted hydrocarbon group having 1 to 20 carbon and optionally up to 6 heteroatoms, such as a substituted or unsubstituted, linear or branched alkyl, alkenyl or alkynyl group having up to 20, such as up to 12 carbon atoms, such as methyl, ethyl, propyl, butyl, pentyl, hexyl, heptyl, octyl, nonyl or decyl, or one of the above alkyls substituted with an aryl group, or is substituted at the terminal carbon atom.

In various embodiments, $R^1$ or $R^2$ is H and the other group is a straight-chain or branched, saturated or unsaturated, substituted or unsubstituted hydrocarbon group having 1 to 20 carbon atoms and optionally up to 6 heteroatoms, such as a linear or branched alkyl, alkenyl or alkynyl group having up to 20, such as up to 12 carbon atoms. In various embodiments, $R^1$ and $R^2$ may also be H.

When R and $R^1$ combine with one another in order to form a cyclic group, this cyclic group is selected from substituted or unsubstituted aryl having up to 20, such as up to 12, carbon atoms, substituted or unsubstituted heteroaryl having up to 20, such as up to 12, carbon atoms, and 1 to 6, such as 1 to 4, heteroatoms selected from O, S and N, substituted or unsubstituted cycloalkyl or cycloalkenyl having up to 20, such as up to 12, carbon atoms, and substituted or unsubstituted heterocycloalkyl or heterocycloalkenyl having up to 20, such as up to 12, carbon atoms, and 1 to 6, such as 1 to 4, heteroatoms selected from O, S and N, such as cycloalkyl or cycloalkenyl as defined above.

Generally, in various embodiments, it is that R, $R^1$, and $R^2$ be selected to form, together with the two carbon atoms to which they are attached, an organic group having at least 6 carbon atoms.

In various embodiments, $R^1$ and $R^2$ are H and R is a such as linear, optionally substituted, alkyl group having up to 12 carbon atoms. When substituted, the substituent is a cyclic group, for example an aryl or heteroaryl ring, a cycloalkyl or heterocycloalkyl group, such as having 5-6 carbon atoms.

Unless explicitly stated otherwise, "substituted" as used herein means that one or more hydrogen atoms in the corresponding group are replaced by another group, such as selected from hydroxyl, carboxyl, amino, halogen, (hetero)alkyl, (hetero)alkenyl, (hetero)alkynyl, (hetero)aryl, (hetero)cycloalkyl, and (hetero)cycloalkenyl, with the proviso that a given group may not be substituted with a similar group (i.e. for example, alkyl with alkyl). Non-limiting examples are alkylaryl or arylalkyl groups.

"Groups" of the above-mentioned odoriferous ketones and aldehydes are the corresponding enols in which the hydroxyl group is replaced by the heterocycles having the formula given above, bound via the nitrogen atom. In this case, A is a cyclic, such as aromatic, hydrocarbon group which contains at least one nitrogen atom in the cycle and binds via this nitrogen atom to the rest of the molecule, wherein in A further carbon atoms can be replaced with N, O, or S, and at least one Hydrogen atom of A may be substituted with a substituent X, wherein X is selected from —F, —Cl, —Br, —NO$_2$, —OH, =O, —CH$_3$, —CH$_2$CH$_3$.

In a non-limiting embodiment, A is composed of one or more 5- or 6-membered rings, which may be present as spiro compounds, ring assemblies, condensed polycyclic compounds, and bridged polycyclic compounds. In a non-limiting embodiment, A is composed of one to three 5- or 6-membered rings, in particular of condensed polycyclic compounds.

A is selected from the group of the following substituted or unsubstituted compounds: pyrazole, imidazole, benzimidazole, imidazoline, indole, quinoline, isoquinoline, purine, pyrimidine, oxazole, thiazole, 1,4-thiazine, xanthine, triazole and tetrazole, wherein the at least one substituent is selected from —F, —Cl, —Br, —NO$_2$, —OH, =O, —CH$_3$, —CH$_2$CH$_3$, such as the compound is imidazole, imidazoline or pyrimidine.

The heterocycles are characterized by good stability to hydrolysis and can also be used in aqueous media or in production processes for granules, without suffering excessive loss of activity. In this way, liquid washing and cleaning agents such as liquid detergents, fabric softeners, hand dishwashing detergents, hard surface cleaners, floor wipes, etc. are also conceivable, as are solid washing and cleaning agents, for example textile detergent granules, automatic dishwashing detergents or cleaning and scouring agents. Likewise, the heterocycles can be used in cosmetic agents for skin and hair treatment. Here, too, both liquid agents, such as showering/bathing products, deodorants and hair shampoo, as well as solid agents, such as soap bars, are meant.

Due to the excellent suitability of the compounds for use in washing and cleaning agents, the use of heterocycles as described above as fragrance in liquid or solid washing and cleaning agents and in cosmetic agents, in particular those for skin and hair treatment, but also air care agents and insect repellents, is another object.

Depending on the nature and intended use of the agents to be fragranced, the heterocycles can be introduced in varying amounts. Usually, the heterocycles are used in washing and cleaning agents in amounts of 0.001 to 5 wt. %, such as 0.01 to 2 wt. %, in each case based on the agent concerned. The agents may include one heterocycle or more, different heterocycles as described herein, wherein the above amounts refer to the total amount of all heterocycles. In insect repellents, the amounts used can be significantly higher, for example, concentrations of 0.001 to 100 wt. %, such as 1 to 50 wt. %, in each case based on the agent, are used here.

The heterocycles can be used as the sole fragrance, but it is also possible to use fragrance mixtures which consist only in part of the heterocycles. Such mixtures have the advantage that the components of the fragrance mixture, which are not present as heterocycles of odoriferous ketones or aldehydes, can also be improved in terms of the durability of the fragrance impression. Thus, in particular fragrance mixtures can be used which contain 1 to 50 wt. %, such as 5 to 40 and in particular at most 30 wt. % of heterocycles based on the fragrance mixture. In other embodiments, in which in particular the delayed fragrance effect of the heterocycles is to be used, in the use, advantageously at least 30 wt. %, such as at least 40 wt. % and in particular at least 50 wt. % of the total perfume contained in the agent are introduced into the agent via the heterocycles, while the remaining 70 wt. %, such as 60 wt. % and in particular 50 wt. % of the total perfume contained in the agent is sprayed on in a conventional manner or otherwise introduced into the agent. The use can therefore advantageously be characterized in that the heterocycles are used together with other fragrances.

By dividing the total perfume content of the agent into perfume which is contained in the heterocycles and perfume conventionally incorporated, a variety of product characteristics can be realized which become possible only by the use. Thus, for example, it is conceivable and possible to divide the total perfume content of the agent into two portions, x and y, wherein the proportion x consists of adherent, i.e. less volatile, perfume oils and the portion y consists of more volatile perfume oils.

It is now possible to produce, for example, washing or cleaning agents in which the proportion of the perfume, which is introduced into the agent via the heterocycles, is composed mainly of adherent odorants. In this way, adherent odorants intended to fragrance the treated articles, in particular textiles, can be "retained" in the product and their action can develop as a result mainly on the treated laundry. In contrast, the more volatile odorants contribute to a more intensive fragrancing of the agent per se. In this way, it is also possible to produce washing and cleaning agents which have as an agent an odor which differs from the odor of the treated articles. There are hardly any limits to the creativity of perfumers, since both the choice of odorants and the choice of method of incorporation into the agent offer virtually limitless possibilities for fragrancing the agent and to fragrance the articles by means of the agent intended to treat them.

Of course, the principle described above can also be reversed by incorporating the more volatile odorants into the heterocycles and by spraying or otherwise incorporating the less volatile, adherent odorants onto the agents. In this way, the loss of the more volatile odorants from the packaging during storage and transport is minimized, while the fragrance characteristic of the agents is determined by the more adherent perfumes.

The only limit of this procedure is that the fragrances which are to be introduced via the heterocycles come from the group of odoriferous ketones and/or aldehydes. The fragrances incorporated into the agents in a conventional manner are not subject to any restrictions. Individual odorant compounds, such as the synthetic products of the ester, ether, aldehyde, ketone, alcohol, and hydrocarbon types, can be used as perfume oils or fragrances. Odorant compounds of the ester type are, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate, and jasmacyclate. The ethers include, for example, benzyl ethyl ether and Ambroxan; the aldehydes include, for example, the linear alkanals having 8-18 C atoms, citral, citronellal, citronellyloxyacetaldehyde, cyclamenaldehyde, Lilial, and bourgeonal; the ketones include, for example, the ionones, α-isomethylionone, and methyl cedryl ketone; the alcohols include anethole, citronellol, eugenol, geraniol, linalool, phenylethyl alcohol, and terpineol; and the hydrocarbons include principally the terpenes such as limonene and pinene. In a non-limiting embodiment, however, mixtures of different odorants are used, which together produce an appealing fragrance note.

Perfume oils of this type may also contain natural odorant mixtures which can be obtained from plant sources such as pine, citrus, jasmine, patchouli, rose or ylang-ylang oil. Clary sage oil, chamomile oil, clove oil, melissa oil, mint oil, cinnamon leaf oil, lime blossom oil, juniper berry oil, vetiver oil, olibanum oil, galbanum oil, labdanum oil and orange blossom oil, neroli oil, orange peel oil and sandalwood oil are also suitable.

The general description of perfumes that can be used (see above) generally represents the different substance classes of odorants. In order to be perceptible, an odorant must be volatile, wherein, in addition to the nature of the functional groups and the structure of the chemical compound, the molar mass also plays an important role. Therefore, most odorants have molar masses of up to approximately 200 daltons, whereas molar masses of 300 daltons and above represent something of an exception. Due to the differing volatility of odorants, the odor of a perfume or fragrance composed of multiple odorants varies over the course of vaporization, wherein the odor impressions are divided into "top note," "middle note or body" and "end note or dry out." Because the perception of an odor also depends to a large extent on the odor intensity, the top note of a perfume or fragrance does not only consist of highly volatile compounds, while the end note consists for the most part of less volatile, i.e. adherent, odorants. When composing perfumes, more volatile odorants can be bound, for example, to specific fixatives, thereby preventing them from evaporating too quickly. The above-described embodiment, in which the more-volatile odorants or fragrances are present in the heterocycles, is one such method for fixing odorants. The subdivision below of odorants into "more volatile" and "adherent" odorants is therefore not a statement with regard to the odor impression, and, moreover, as to whether the corresponding odorants is perceived as a top or middle note.

Adherent odorants that can be used in various embodiments are, for example, essential oils such as angelica root oil, anise oil, arnica blossom oil, basil oil, bay oil, champaca blossom oil, abies alba oil, abies alba cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, lavender oil, lemon grass oil, lime oil, mandarin oil, melissa oil, ambrette seed oil, myrrh oil, clove oil, neroli oil, niaouli oil, olibanum oil, origanum oil, palmarosa oil, patchouli oil, Peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil, and cypress oil. However, higher-boiling and solid odorants of natural or synthetic origin may also be used as adherent odorants or odorant mixtures, i.e. fragrances. These compounds include the compounds stated in the following and mixtures thereof: Ambrettolide, Ambroxan, a-amylcinnamaldehyde, anethole, anisaldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerianate, borneol, bornyl acetate, boisambrene forte, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, methylanthranilic acid methyl ester, p-methylacetophenone, methyl chavicol, p-methylquinoline, methyl-β-naphthyl ketone, methyl n-nonyl acetaldehyde, methyl n-nonyl ketone, muscone, β-naphthol ethyl ether, P-naphthol methyl ether, nerol, n-nonyl aldehyde, nonyl alcohol, n-octylaldehyde, p-oxyacetophenone, pentadecanolide, β-phenethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, sandelice, skatole, terpineol, thymene, thymol, troenan, γ-undecalactone, vanillin, veratraldehyde, cinnamaldehyde, cinnamyl alcohol, cinnamic acid, cinnamic acid ethyl ester, cinnamic acid benzyl ester.

More volatile odorants include in particular lower-boiling odorants of natural or synthetic origin, which may be used alone or in mixtures. Examples of more volatile odorants are diphenyl oxide, limonene, linalool, linalyl acetate and propionate, melusate, menthol, menthone, methyl-n-heptenone, pinene, phenylacetaldehyde, terpinyl acetate, citral and citronellal.

In addition to the described fragrances, the agents, such washing and cleaning agents, can, of course, contain customary ingredients of agents of this kind. In washing and cleaning agents, primarily surfactants, builders, bleaching agents, enzymes, and other active substances should be mentioned in this regard. The essential ingredients of washing and cleaning agents include in particular surfactants.

Depending on the intended purpose of the agents, the surfactant content will be selected so as to be higher or lower. Usually, the surfactant content of washing agents is between 10 and 40 wt. %, such as between 12.5 and 30 wt. %, and in particular between 15 and 25 wt. %, while cleaning agents for automatic dishwashing contain between 0.1 and 10 wt. %, such as between 0.5 and 7.5 wt. %, and in particular between 1 and 5 wt. % surfactants.

These surface-active substances come from the group of anionic, non-ionic, zwitterionic or cationic surfactants, wherein anionic and non-ionic surfactants are for economical reasons and due to the performance spectrum thereof during washing and cleaning.

Anionic surfactants that are used are those of the sulfonate and sulfate types, for example. Surfactants of the sulfonate type that are considered are in this case $C_{9-13}$ alkylbenzene sulfonates, olefin sulfonates, i.e. mixtures of alkene and hydroxyalkane sulfonates, and disulfonates, as they are obtained, for example, from $C_{12-18}$ monoolefins having a terminal or internal double bond by way of sulfonation with gaseous sulfur trioxide and subsequent alkaline or acid hydrolysis of the sulfonation products. Alkane sulfonates obtained from $C_{12-18}$ alkanes, for example by way of sulfochlorination or sulfoxidation with subsequent hydrolysis or neutralization, are also suitable. Likewise, the esters of α-sulfofatty acids (ester sulfonates) are suitable, for example the a-sulfonated methyl esters of hydrogenated coconut fatty acids, palm kernel fatty acids or tallow fatty acids.

Sulfated fatty acid glycerol esters are further suitable anionic surfactants. Fatty acid glycerol esters are understood to mean the monoesters, diesters and triesters and the mixtures thereof, as they are obtained during production by way of esterification of a monoglycerol having 1 to 3 mol of fatty acid or during the transesterification of triglycerides having 0.3 to 2 mol of glycerol. Non-limiting sulfated fatty acid glycerol esters are in this case the sulfation products of saturated fatty acids having 6 to 22 carbon atoms, for example of caproic acid, caprylic acid, capric acid, myristic acid, lauric acid, palmitic acid, stearic acid or behenic acid.

The alkali salts and in particular the sodium salts of the sulfuric acid half-esters of $C_{12}$-$C_{18}$ fatty alcohols, for example from coconut fatty alcohol, tallow fatty alcohol, lauryl alcohol, myristyl alcohol, cetyl alcohol or stearyl alcohol, or of $C_{10}$-$C_{20}$ oxo alcohols and the half-esters of secondary alcohols having these chain lengths are as alk(en)yl sulfates. Alk(en)yl sulfates having the described chain length that include a synthetic straight-chain alkyl group prepared on a petrochemical basis, and have a degradation behavior similar to that of the adequate compounds based on fatty chemical raw materials, are also possible. From a washing perspective, the $C_{12}$-$C_{16}$ alkyl sulfates, $C_{12}$-$C_{15}$ alkyl sulfates and $C_{14}$-$C_{15}$ alkyl sulfates are possible.

The sulfuric acid monoesters of straight-chain or branched $C_{7-21}$ alcohols ethoxylated with 1 to 6 mol of ethylene oxide, such as 2-methyl-branched $C_{9-11}$ alcohols having, on average, 3.5 mol ethylene oxide (EO) or $C_{12-18}$ fatty alcohols having 1 to 4 EO, are also suitable. Due to the high foaming behavior thereof, they are used in cleaning agents only in relatively small amounts, for example in amounts of 1 to 5 wt. %.

Further suitable anionic surfactants are also the salts of alkyl sulfosuccinic acid, which are also referred to as sulfosuccinates or as sulfosuccinic acid esters and represent the monoesters and/or diesters of sulfosuccinic acid with alcohols, such as fatty alcohols, and in particular ethoxylated fatty alcohols. Non-limiting sulfosuccinates contain $C_{8-18}$ fatty alcohol groups or mixtures of these. In particular, non-limiting sulfosuccinates contain a fatty alcohol group that is derived from ethoxylated fatty alcohols, which taken alone represent non-ionic surfactants (for description see below). Non-limiting examples, in turn, are sulfosuccinates, the fatty alcohol groups of which derive from ethoxylated fatty alcohols exhibiting a restricted homolog distribution. Likewise, it is also possible to use alk(en)yl succinic acid having 8 to 18 carbon atoms in the alk(en)yl chain, or the salts thereof.

Further anionic surfactants that can also be used are in particular soaps. Saturated fatty acid soaps are suitable, such as the salts of lauric acid, myristic acid, palmitic acid, stearic acid, hydrogenated erucic acid and behenic acid, and in particular soap mixtures derived from natural fatty acids, such as coconut fatty acids, palm kernel fatty acids or tallow fatty acids.

The anionic surfactants, including the soaps, can be present in the form of the sodium, potassium or ammonium salts thereof, or as soluble salts of organic bases, such as monoethanolamine, diethanolamine or triethanolamine. The anionic surfactants are present in the form of the sodium, potassium or magnesium salts thereof, and in particular in the form of the sodium salts.

There are no general conditions that must be adhered to that would stand in the way of having a degree of freedom in terms of the formulation when selecting the anionic surfactants. Non-limiting agents, however, have a soap content that exceeds 0.2 wt. %, based on the total weight of the washing and cleaning agent produced in step d). Non-limiting anionic surfactants to be used are the alkylbenzene sulfonates and fatty alcohol sulfates, wherein shaped detergent bodies contain 2 to 20 wt. %, such as from 2.5 to 15 wt. %, and in particular 5 to 10 wt. % fatty alcohol sulfate(s), in each case based on the weight of the agents.

Alkoxylated, advantageously ethoxylated, in particular primary alcohols having 8 to 18 C atoms and, on average, 1 to 12 mols of ethylene oxide (EO) per mol of alcohol, are used as non-ionic surfactants, in which the alcohol group can be linear or methyl-branched in the 2 position, or can contain linear and methyl-branched groups in the mixture, as are usually present in oxo alcohol groups. However, alcohol ethoxylates having linear groups of alcohols of native origin having 12 to 18 C atoms, for example of coconut, palm, tallow fatty or oleyl alcohol, and an average of 2 to 8 EO per mol of alcohol, are usable. Non-limiting ethoxylated alcohols include, for example, $C_{12-14}$ alcohols having 3 EO or 4 EO, $C_{9-11}$ alcohol having 7 EO, $C_{13-15}$ alcohols having 3 EO, 5 EO, 7 EO or 8 EO, $C_{12-18}$ alcohols having 3 EO, 5 EO or 7 EO, and mixtures thereof, such as mixtures of $C_{12-14}$ alcohol having 3 EO and $C_{12-18}$ alcohol having 5 EO. The degrees of ethoxylation indicated represent statistical averages that can correspond to an integer or a fractional number for a specific product. Non-limiting alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO.

Another class of non-ionic surfactants that are used, which are used either as the sole non-ionic surfactant or in combination with other non-ionic surfactants, is alkoxylated, such as ethoxylated or ethoxylated and propoxylated fatty acid alkyl esters, such as having 1 to 4 carbon atoms in the alkyl chain, in particular fatty acid methyl esters, such as those described for example in the Japanese patent application JP 58/217598 or those prepared according to the method described in the international patent application WO-A-90/13533.

Another class of non-ionic surfactants that can advantageously be used is the alkyl polyglycosides (APG). Alkyl polyglycosides that can be used have the general formula $RO(G)_z$, in which R represents a linear or branched, in particular methyl-branched at the 2-position, saturated or unsaturated aliphatic group having 8 to 22, such as 12 to 18, C atoms, and G is the symbol that represents a glycose unit having 5 or 6 C atoms, such as glucose. The degree of glycosidation z is between 1.0 and 4.0, such as between 1.0 and 2.0, and in particular between 1.1 and 1.4. Linear alkyl polyglycosides are such as used, in other words alkyl polyglycosides in which the polyglycol group is a glucose group and the alkyl group is an n-alkyl group.

Non-ionic surfactants of the amine oxide type, for example N-cocoalkyl-N,N-dimethylamine oxide and N-tallow-alkyl-N,N-dihydroxyethylamine oxide, and of the fatty acid alkanolamides can also be suitable. The quantity of these non-ionic surfactants is no more than that of the ethoxylated fatty alcohols, in particular no more than half thereof.

Further suitable surfactants are polyhydroxy fatty acid amides of formula (III),

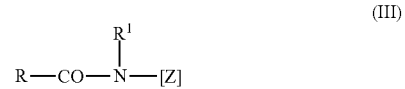

(III)

in which RCO represents an aliphatic acyl group having 6 to 22 carbon atoms, $R^1$ represents hydrogen, an alkyl or hydroxyalkyl group having 1 to 4 carbon atoms, and [Z] represents a linear or branched polyhydroxyalkyl group having 3 to 10 carbon atoms and 3 to 10 hydroxyl groups. The polyhydroxy fatty acid amides are known substances that can usually be obtained by the reductive amination of a reducing sugar with ammonia, an alkylamine or an alkanolamine, and subsequent acylation with a fatty acid, a fatty acid alkyl ester or a fatty acid chloride.

The group of polyhydroxy fatty acid amides also includes compounds of formula (IV),

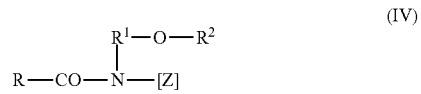

(IV)

in which R represents a linear or branched alkyl or alkenyl group having 7 to 12 carbon atoms, $R^1$ represents a linear, branched or cyclic alkyl group or an aryl group having 2 to 8 carbon atoms, and $R^2$ represents a linear, branched or cyclic alkyl group or an aryl group or an oxy alkyl group having 1 to 8 carbon atoms, wherein $C_{1-4}$ alkyl or phenyl groups are possible, and [Z] represents a linear polyhydroxy alkyl group, the alkyl chain of which is substituted with at least two hydroxyl groups, or alkoxylated, such as ethoxylated or propoxylated derivatives of this group. [Z] is obtained by the reductive amination of a reduced sugar, for example glucose, fructose, maltose, lactose, galactose, mannose or xylose. The N-alkoxy-substituted or N-aryloxy-substituted compounds can be converted, in the presence of an alkoxide as the catalyst, into the desired polyhydroxy fatty acid amides by reacting these with fatty acid methyl esters, for example according to the teaching of the international application WO-A-95/07331.

Builders are another significant group of washing and cleaning agent ingredients. This substance class is understood to cover both organic and inorganic builders. These are compounds which may carry out a carrier function in the agents and also act as a water softening substance during use.

Usable organic builders are, for example, the polycarboxylic acids that can be used in the form of the sodium salts thereof, polycarboxylic acids being understood to mean those carboxylic acids that carry more than one acid function. These include, for example, citric acid, adipic acid, succinic acid, glutaric acid, malic acid, tartaric acid, maleic acid, fumaric acid, saccharic acids, aminocarboxylic acids, nitrilotriacetic acid (NTA), provided that the use thereof is not objectionable for ecological reasons, and mixtures thereof. Non-limiting salts are the salts of polycarboxylic acids such as citric acid, adipic acid, succinic acid, glutaric acid, tartaric acid, saccharic acids, methylglycinediacetic acid, glutamine diacetic acid, and mixtures thereof. The acids can also be used per se. In addition to the builder effect thereof, the acids typically also have the property of being an acidification component and are thus also used, for example in the granules, for setting a lower and milder pH of washing or cleaning agents. Particularly noteworthy here are citric acid, succinic acid, glutaric acid, adipic acid, gluconic acid, methylglycinediacetic acid, glutamine diacetic acid and any mixtures thereof.

Polymeric polycarboxylates are also suitable as builders. These are, for example, the alkali metal salts of polyacrylic acid or polymethacrylic acid, for example those having a relative molecular mass of 500 to 70,000 g/mol. This substance class has already been described in detail above. The (co)polymeric polycarboxylates may be used either as a powder or an aqueous solution. The content of (co)polymeric polycarboxylates in the agent is 0.5 to 20 wt. %, in particular 3 to 10 wt. %.

To improve water solubility, the polymers can also contain allyl sulfonic acids, such as allyloxybenzene sulfonic acid and methallyl sulfonic acid, as in EP-B-0 727 448 for example, as monomer. Biodegradable polymers composed of more than two different monomer units are also usable herein, for example those that, according to DE-A-43 00 772, contain salts of acrylic acid and of maleic acid, and vinyl alcohol or vinyl alcohol derivatives as monomers or, according to DE-C-42 21 381, salts of acrylic acid and of 2-alkylallylsulfonic acid and sugar derivatives as monomers. Further non-limiting copolymers are those that are described in the German patent applications DE-A-43 03 320 and DE-A-44 17 734 and comprise acrolein and acrylic acid/acrylic acid salts or acrolein and vinyl acetate as monomers. Polymeric aminodicarboxylic acids, the salts thereof or the precursors thereof should likewise be mentioned as further non-limiting builders. Non-limiting examples are polyaspartic acids or the salts and derivatives thereof, of which it is disclosed in the German patent application DE-A-195 40 086 that they also exhibit a bleach-stabilizing effect in addition to cobuilder properties.

Additional suitable builders are polyacetals, which may be obtained by reacting dialdehydes with polyolcarboxylic acids which have 5 to 7 C atoms and at least 3 hydroxyl groups, for example as described in the European patent application EP-A-0 280 223. Non-limiting polyacetals are obtained from dialdehydes such as glyoxal, glutaraldehyde, terephthalaldehyde and mixtures thereof, and from polyol carboxylic acids such as gluconic acid and/or glucoheptonic acid.

Further suitable organic builders are dextrins, for example oligomers or polymers of carbohydrates, which can be obtained by the partial hydrolysis of starches. The hydrolysis can be carried out according to customary methods, for example acid- or enzyme-catalyzed methods. These dextrins are hydrolysis products having average molar masses in the range of 400 to 500,000 g/mol. In this case, a polysaccharide having a dextrose equivalent (DE) in the range of 0.5 to 40, in particular 2 to 30 is possible, DE being a common measure of the reducing action of a polysaccharide compared to dextrose, which has a DE of 100. It is possible to use both maltodextrins having a DE between 3 and 20 and dried glycose syrups having a DE between 20 and 37, and what are known as yellow dextrins and white dextrins having higher molar masses in the range of 2000 to 30,000 g/mol. A non-limiting dextrin is described in the British patent application 94 19 091. Oxidized derivatives of dextrins of this type are the reaction products thereof having oxidizing agents which are capable of oxidizing at least one alcohol function of the saccharide ring to form a carboxylic acid function. Oxidized dextrins of this kind and methods for the preparation thereof are known, for example, from the European patent applications EP-A-0 232 202, EP-A-0 427 349, EP-A-0 472 042 and EP-A-0 542 496, and the international patent applications WO 92/18542, WO-A-93/08251, WO-A-93/16110, WO-A-94/28030, WO-A-95/07303, WO-A-95/12619 and WO-A-95/20608. An oxidized oligosaccharide according to the German patent application DE-A-196 00 018 is also suitable. A product that is oxidized on $C_6$ of the saccharide ring can be particularly advantageous.

Oxydisuccinates and other derivatives of disuccinates, such as ethylenediamine disuccinate, are further suitable cobuilders. Ethylenediamine-N,N'-disuccinate (EDDS), the synthesis of which is described in U.S. Pat. No. 3,158,615, for example, is used in the form of the sodium or magnesium salts thereof. Glycerol disuccinates and glycerol trisuccinates, as described for example in the US patent specifications U.S. Pat. Nos. 4,524,009, 4,639,325, in the European patent application EP-A-0 150 930 and in the Japanese patent application JP 93/339896, are also furthermore usable in this context. Suitable use amounts are 3 to 15 wt. % in zeolite-containing and/or silicate-containing formulations.

Further suitable organic cobuilders are, for example, acetylated hydroxycarboxylic acids or the salts thereof, which optionally can also be present in lactone form and comprise at least 4 carbon atoms and at least one hydroxy group, as well as no more than two acid groups. Cobuilders of this kind are described, for example, in the international patent application WO-A-95/20029.

A further substance class having cobuilder properties is that of phosphonates. These include, in particular, hydroxyalkane and aminoalkane phosphonates. Among the hydroxyalkanephosphonates, 1-hydroxyethane-1,1-diphosphonate (HEDP) is of particular importance as a cobuilder. It is used as a sodium salt, the disodium salt reacting neutral and the tetrasodium salt reacting alkaline (pH 9). Possible aminoalkane phosphonates include ethylenediamine tetramethylene phosphonate (EDTMP), diethylentriamine pentamethylene phosphonate (DTPMP) and the higher homologs thereof. They are used in the form of the neutrally reacting sodium salt, for example as the hexasodium salt of EDTMP or as the hepta- and octa-sodium salt of DTPMP. From the class of phosphonates, HEDP is used as a builder. The aminoalkane phosphonates additionally have a pronounced heavy-metal-binding ability. Accordingly, it may be possible, in particular if the agents also include bleach, to use aminoalkane phosphonates, in particular DTPMP, or to use mixtures of the above-mentioned phosphonates.

Moreover, all compounds that are able to form complexes with alkaline earth ions can be used as cobuilders.

A used inorganic builder is finely crystalline, synthetic and bound water-containing zeolite. The microcrystalline, synthetic and bound water-containing zeolite used is zeolite A and/or zeolite P. Zeolite X and mixtures of A, X and/or P, for example a co-crystallizate from zeolites A and X are also suitable, however. The zeolite can be used as a spray-dried powder or also as an undried, stabilized suspension that is still moist from production. If zeolite is used in the form of a suspension, it may contain small additional additions of non-ionic surfactants as stabilizers, for example 1 to 3 wt. %, based on the zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups or ethoxylated isotridecanols. Suitable zeolites have an average particle size of less than 10 μm (volume distribution; measuring method: Coulter counter) and contain 18 to 22 wt. %, and in particular 20 to 22 wt. %, of bound water. In embodiments, zeolites are contained in the premix in amounts of 10 to 94.5 wt. %, such as for zeolite to be contained in amounts of from 20 to 70 wt. %, in particular from 30 to 60 wt. %.

Suitable partial substitutes for zeolites are phyllosilicates of natural and synthetic origin. Phyllosilicates of this kind are known from patent applications DE-A-23 34 899, EP-A-0 026 529 and DE-A-35 26 405, for example. The usability thereof is not limited to a specific composition or structural formula. However, smectites, in particular bentonites, are possible here. Crystalline, layered sodium silicates of the general formula $NaMSi_xO_{2x+1} \cdot yH_2O$, where M is sodium or hydrogen, x is a number from 1.9 to 4 and y is a number from 0 to 20, and non-limiting values for x are 2, 3 or 4, are also suitable as zeolite or phosphate substitutes. Crystalline phyllosilicates of this kind are described, for example, in European patent application EP-A-0 164 514. Non-limiting crystalline phyllosilicates of the formula provided are those in which M represents sodium and x assumes the values 2 or 3. In particular, both 3- and 6-sodium disilicates ($Na_2Si_2O_5 \cdot yH_2O$) are possible.

The builders also include amorphous sodium silicates having a $Na_2O$ modulus: $SiO_2$ of 1:2 to 1:3.3, such as from 1:2 to 1:2.8 and in particular of 1:2 to 1:2.6, which are delayed in dissolution and have secondary washing properties. Compared to conventional amorphous sodium silicates, the delayed dissolution may have been caused in a variety of ways, for example by way of surface treatment, compounding, compacting/compression or over-drying. As used herein, the term "amorphous" is also understood to mean "X-ray amorphous." This means that in X-ray diffraction experiments, the silicates do not supply any sharp X-ray reflexes, as are typical of crystalline substances, but at best one or more maxima of the scattered X-rays, which have a width of several degree units of the diffraction angle. However, even particularly good builder properties may very well be achieved when the silicate particles supply washed-out or even sharp diffraction maxima in electron diffraction experiments. This should be interpreted such that the products comprise microcrystalline regions measuring 10 to several hundred nm, values up to a maximum of 50 nm, and in particular up to a maximum of 20 nm, being possible. X-ray amorphous silicates of this kind, which likewise exhibit delayed dissolution compared with conventional water glasses, are described in the German patent application DE-A-44 00 024, for example. In particular, compressed/compacted amorphous silicates, compounded amorphous silicates and overdried X-ray amorphous silicates are possible, in particular the overdried silicates also occurring as carriers in the granules or being used as carriers in the method.

Of course, it is also possible to use the generally known phosphates as builders, provided that such use should not be avoided for ecological reasons. Sodium salts of orthophosphates, pyrophosphates and in particular tripolyphosphates are particularly suitable. The content thereof is generally no more than 25 wt. %, such as no more than 20 wt. %, in each case based on the finished agent. In embodiments, the agents are phosphate-free, i.e. contain less than 1 wt. % of such phosphates.

In addition to the aforementioned components, the washing and cleaning agents can additionally contain one or more of the substances from the group of bleaching agents, bleach activators, enzymes, pH adjusters, fluorescing agents, dyes, suds suppressors, silicone oils, anti-redeposition agents, optical brighteners, graying inhibitors, dye transfer inhibitors, corrosion inhibitors and silver protecting agents. Suitable agents are known in the prior art.

This list of washing and cleaning agent ingredients is by no means exhaustive, but merely reflects the most essential typical ingredients of agents of this kind. In particular, if the preparations are liquid or gel-like, organic solvents can also be contained in the agents. These are monohydric or polyhydric alcohols having 1 to 4 carbon atoms. Non-limiting alcohols in such agents are ethanol, 1,2-propanediol, glycerol, and mixtures of these alcohols. In non-limiting embodiments, agents of this type contain 2 to 12 wt. % of alcohols of this kind.

In principle, the agents can exhibit different physical states. In a non-limiting embodiment, the washing or cleaning agents are liquid or gel-like agents, in particular liquid detergents or liquid dishwashing detergents or cleaning gels, it also being possible for these to be in particular gel-like cleaning agents for flushing toilets. Such gel-like cleaning agents for flushing toilets are described, for example, in the German patent application DE-A-197 158 72.

Further typical cleaning agents that may include the heterocyclene are liquid or gel-like cleaners for hard surfaces, in particular those known as all-purpose cleaners, glass cleaners, floor or bathroom cleaners, and specific embodiments of such cleaners, which also include acid or alkaline forms of all-purpose cleaners, as well as glass cleaners having what is known as anti-rain action. These liquid cleaning agents can be present either in one or in multiple phases. In a non-limiting embodiment, the cleaners have two different phases.

In the broadest sense, "cleaner" is a designation for formulations which usually contain surfactants and have a very wide range of use, and, as a result, a widely varying composition. The most important market segments are household cleaners, industrial (technical) and institutional cleaners. Based on the pH value, a distinction is made between alkaline, neutral and acid cleaners, and according to the form in which the product is offered, a distinction is made between liquid and solid cleaners (including in tablet form). Contrary to dishwashing agents, for example, which can likewise be categorized in the cleaner product group, cleaners for hard surfaces exhibit an optimal application profile, both in the concentrated state and in a diluted aqueous solution, in conjunction with mechanical energy. Cold cleaners develop their action without an increased temperature. Above all, surfactants and/or alkali carriers, alternatively acids, optionally also solvents such as glycol ethers and lower alcohols, are decisive for the cleaning effect. In general, the formulations also include builders, and, depending on the type of cleaner, also bleaching agents, enzymes, microbe-mitigating or disinfecting additives, perfume oils and dyes. Cleaners can also be formulated as microemulsions. To a large degree, the cleaning success depends on the type of dirt, which also varies widely geographically, and the properties of the surfaces to be cleaned.

The cleaners can contain anionic, non-ionic, amphoteric or cationic surfactants or surfactant mixtures of one, a several or all of these surfactant classes as the surfactant component. The cleaners contain surfactants in amounts, based on the composition, of 0.01 to 30 wt. %, such as from 0.1 to 20 wt. %, for example from 1 to 14 wt. %, or from 3 to 10 wt. %.

Suitable non-ionic surfactants in all-purpose cleaners of this kind are, for example, $C_8$-$C_{18}$ alkyl alcohol polyglycol ethers, alkyl polyglycosides and nitrogen-containing surfactants and mixtures thereof, in particular of the first two. The agents contain non-ionic surfactants in amounts, based on the composition, of 0 to 30 wt. %, such as from 0.1 to 20 wt. %, for example from 0.5 to 14 wt. %, or from 1 to 10 wt. %.

$C_{8-18}$ alkyl alcohol polypropylene glycol/polyethylene glycol ethers represent known non-ionic surfactants. They can be described by the formula $R^iO$—$(CH_2CH(CH_3)O)_p$ $(CH_2CH_2O)_e$—H, in which $R^i$ represents a linear or branched aliphatic alkyl and/or alkenyl group having 8 to 18 carbon atoms, p represents 0 or numbers from 1 to 3, and e represents numbers from 1 to 20. The $C_{8-18}$ alkyl alcohol polyglycol ethers can be obtained by adding propylene oxide and/or ethylene oxide to alkyl alcohols, such as fatty alcohols. Typical examples are polyglycol ethers in which $R^1$ represents an alkyl group having 8 to 18 carbon atoms, p represents 0 to 2, and e represents numbers from 2 to 7. Non-limiting representatives are, for example, $C_{10}$-$C_{14}$ fatty alcohol+1 PO+6EO ether (p=1, e=6), and $C_{12}$-$C_{18}$ fatty alcohol+7EO ether (p=0, e=7) and the mixtures thereof.

It is also possible to use end-capped $C_8$-$C_{18}$ alkyl alcohol polyglycol ethers, i.e. compounds in which the free OH group is etherified. The end-capped $C_{8-18}$ alkyl alcohol polyglycol ethers can be obtained by relevant methods of preparative organic chemistry. $C_{8-18}$ alkyl alcohol polyglycol ethers are reacted, in the presence of bases, with alkyl halides, in particular butyl or benzyl chloride. Typical examples are mixed ethers, in which $R^i$ represents a technical fatty alcohol group, a $C_{12/14}$ coconut alkyl group, p represents 0, and e represents 5 to 10, which are capped with a butyl group.

Furthermore, non-limiting non-ionic surfactants are the alkyl polyglycosides already described above.

Nitrogen-containing surfactants may be present as further non-ionic surfactants, such as fatty acid polyhydroxyamides, for example glucamides and ethoxylates of alkylamines, vicinal diols and/or carboxylic acid amides that include alkyl groups having 10 to 22 carbon atoms, such as from 12 to 18 carbon atoms. The degree of ethoxylation of these compounds is generally between 1 and 20, such as between 3 and 10. Non-limiting examples are ethanolamide derivatives of alkanoic acids having 8 to 22 carbon atoms, such as from 12 to 16 carbon atoms. Particularly suitable compounds include lauric acid, myristic acid and palmitic acid monoethanolamides.

Suitable anionic surfactants for all-purpose cleaners are $C_{8-18}$ alkyl sulfates, $C_{8-18}$ alkyl ether sulfates, i.e. the sulfation products of alcohol ethers and/or $C_{8-18}$ alkylbenzenesulfonates, but also $C_{8-18}$ alkanesulfonates, $C_{8-18}$ α-olefinsulfonates, sulfonated $C_{8-18}$ fatty acids, in particular dodecyl benzene sulfonate, $C_{8-22}$ carboxylic acid amide ether sulfates, sulfonosuccinic mono- and di-$C_{1-12}$ alkyl esters, $C_{8-18}$ alkyl polyglycol ether carboxylates, $C_{8-18}$ N-acyl taurides, $C_{8-18}$ N-sarcosinates and $C_{8-18}$ alkyl isethionates or mixtures thereof. They are used in the form of the alkali metal and alkaline-earth metal salts thereof, in particular sodium, potassium and magnesium salts, and ammonium- and mono-, di-, tri- or tetra-alkyl ammonium salts, and, in the case of the sulfonates, also in the form of the corresponding acid thereof, such as dodecylbenzene sulfonic acid. The agents contain anionic surfactants in amounts, based on the composition, of 0 to 30 wt. %, such as from 0.1 to 20 wt. %, for example 1 to 14 wt. %, or 2 to 10 wt. %.

Due to the foam-controlling properties thereof, the all-purpose cleaners can also contain soaps, i.e. alkali or ammonium salts of saturated or unsaturated $C_{6-22}$ fatty acids. The soaps may be used in an amount of up to 5 wt. %, such as from 0.1 to 2 wt. %.

Suitable amphoteric surfactants are, for example, betaines of formula $(R^{ii})(R^{iii})(R^{iv})N^+CH_2COO^-$, in which $R^{ii}$ represents an alkyl group, which is optionally interrupted by heteroatoms or heteroatom groups, having 8 to 25, such as from 10 to 21, carbon atoms, and $R^{iii}$ and $R^{iv}$ represent identical or different alkyl groups having 1 to 3 carbon atoms, in particular $C_{10-18}$ alkyl dimethyl carboxymethyl betaine and $C_{11-17}$ alkyl amido propyl dimethyl carboxymethyl betaine. The agents contain amphoteric surfactants in amounts, based on the composition, of 0 to 15 wt. %, such as from 0.01 to 10 wt. %, or from 0.1 to 5 wt. %.

Suitable cationic surfactants are, inter alia, the quaternary ammonium compounds of formula $(R^v)(R^{vi})(R^{vii})(R^{viii})N^+$ $X^-$, in which $R^v$ to $R^{viii}$ represent four identical or different, and in particular two long-chain and two short-chain, alkyl groups, and $X^-$ represents an anion, in particular a halide ion, for example didecyl dimethyl ammonium chloride, alkyl benzyl didecyl ammonium chloride and the mixtures thereof. The agents contain cationic surfactants in amounts, based on the composition, of 0 to 10 wt. %, such as from 0.01 to 5 wt. %, or from 0.1 to 3 wt. %.

In a non-limiting embodiment, the detergents contain anionic and non-ionic surfactants, together, such as $C_{8-18}$ alkyl benzenesulfonates, $C_{8-18}$ alkyl sulfates and/or $C_{8-18}$ alkyl ether sulfates alongside $C_{8-18}$ Alkylalkoholpolyglykolethers and/or alkyl polyglycosides, in particular $C_{8-18}$ alkyl benzene sulphonates in addition to $C_{8-18}$ alkyl alcohol polyglycol ethers.

The cleaners can also contain builders. Suitable builders are, for example, alkali metal gluconates, citrates, nitrilotriacetates, carbonates and bicarbonates, in particular sodium gluconate, citrate and nitrilotriacetate, and sodium and potassium carbonate and bicarbonate, and alkali metal and alkaline-earth metal hydroxides, in particular sodium and potassium hydroxide, ammonia and amines, in particular monoethanolamine and triethanolamine, and the mixtures thereof. Included here are salts of glutaric acid, succinic acid, adipic acid, tartaric acid and benzene hexacarboxylic acid as well as phosphonates and phosphates. The agents contain builders in amounts, based on the composition, of 0 to 20 wt. %, such as from 0.01 to 12 wt. %, for example from 0.1 to 8 wt. %, or from 0.3 to 5 wt. %, wherein, however, the amount of sodium hexametaphospate, excluding the agents used, is limited to 0 to 5 wt. %. As electrolytes, the builder salts are phase separation agents at the same time.

In addition to the components mentioned, the cleaners may contain further auxiliary agents and additives, as are common in such agents. These include in particular polymers, soil release active ingredients, solvents (e.g. ethanol, isopropanol, glycol ether), solubilizers, hydrotropic substances (e.g. cumene sulfonate, octyl sulfate, butyl glucoside, butyl glycol), cleaning boosters, viscosity regulators (e.g. synthetic polymers such as polysaccharides, polyacrylates, naturally occurring polymers and the derivatives thereof such as xanthan gum, other polysaccharides and/or gelatin), pH regulators (e.g. citric acid, alkanolamines or NaOH), disinfectants, antistatic agents, preservatives, bleaching systems, enzymes, dyes, and opacifiers or skin protection agents, as they are described in EP-A-0 522 506.

The amount of additives of this type in a cleaning agent is usually no greater than 12 wt. %. The lower limit of what is used depends on the additive type and, for dyes, may be as low as 0.001 wt. % or less, for example. The auxiliary content is between 0.01 and 7 wt. %, in particular 0.1 and 4 wt. %.

The pH value of the all-purpose cleaners can be varied across a wide range; however, a range of 2.5 to 12, and in particular 5 to 10.5 is possible. As used herein, the pH value is understood to mean the pH value of the agent in the form of the temporary emulsion.

Such all-purpose cleaner formulations can be modified for arbitrary purposes. One particular embodiment is the glass cleaners. In cleaners of this kind it is essential that stains or outlines remain. In particular, it is a problem in this case that, after cleaning, water condenses on these surfaces and results in what is known as the fogging effect. It is likewise undesirable when what are known as rain stains remain on glass panes exposed to rain. This effect is known as the rain effect or anti-rain effect. These effects can be prevented by suitable additives in glass cleaners.

In another embodiment, the agents are powdery or granular agents. The agents can in this case have any bulk densities. The spectrum of possible bulk densities ranges from low bulk densities of less than 600 g/l, for example 300 g/l, through the range of average bulk densities from 600 to 750 g/l, to the range of high bulk densities of at least 750 g/l.

Arbitrary methods, which are known from the prior art, are suitable for producing such agents.

Further subject matter relates to cosmetic agents for treating hair or skin, which agents contain the heterocycles described herein, such as in the amounts described above in conjunction with the other agents. In a non-limiting embodiment, the cosmetic agents are aqueous preparations that contain active surface-active substances and that are suitable in particular for treating keratin fibers, in particular human hair, or for treating skin.

The hair treatment agents addressed are, in this case, in particular agents for treating human scalp hair. The most common agents of this category can be divided into hair washing agents, hair care agents, hair setting and hair styling agents, hair dyes and hair removal agents. The agents which contain surface-active ingredients and are herein include in particular hair washing agents and hair care agents. These aqueous preparations are typically present in a liquid to pasty form.

Fatty alcohol polyglycol ether sulfates (ether sulfates, alkyl ether sulfates), in part in combination with other usually anionic surfactants, are predominantly used for the most important group of ingredients: the surface-active ingredients or washing-active substances. In addition to good cleaning power and insensitivity to water hardness, shampoo surfactants are intended to have good skin and mucosal compatibility. In accordance with statutory provisions, they have to have good biodegradability. In addition to the alkyl ether sulfates, non-limiting agents can additionally contain further surfactants such as alkyl sulfates, alkyl ether carboxylates, such as having degrees of ethoxylation from 4 to 10, and surfactant protein/fatty acid condensates.

Hair shampoos contain perfume oils to produce a pleasant fragrance note. The shampoos may contain only the heterocycles, but it is also possible if the hair shampoos contain not only these, but also other fragrances. All conventional fragrances permitted in hair shampoos may be used in this case.

The aim of hair care agents is to preserve the natural state of newly regrown hair for as long as possible, and to restore the same if damaged. Features that characterize this natural state are a silky shine, low porosity, a resilient and soft volume, and a pleasantly smooth feel. An important prerequisite for this is a clean, not overly oily scalp that is free of dandruff. Today, hair care agents include a large number of different products, the most important representatives of which are referred to as pre-treatment agents, hair tonics, hairdressing agents, hair rinses and masque products.

The aqueous preparations for treating skin are in particular preparations for human skin care. This care begins with cleansing, for which primarily soaps are used. In this regard, a distinction is made between solid soap, usually in bars, and liquid soap. Accordingly, in a non-limiting embodiment the cosmetic agents are present as shaped bodies that contain surface-active ingredients. In a non-limiting embodiment, the most important ingredients of shaped bodies of this kind are the alkali salts of fatty acids of natural oils and fats, such as having chains of 12 to 18 carbon atoms. Since lauric acid soaps foam particularly well, coconut and palm kernel oils rich in lauric acid are raw materials for fine soap production. The Na salts of fatty acid mixtures are solid; the K salts are slightly pasty. For saponification, the diluted sodium hydroxide solution or potassium hydroxide solution is added to the fat raw materials in a stoichiometric ratio so that an excess of lye of no more than 0.05% is present in the finished soap. In many instances, soaps today are no longer produced directly from the fats, but from the fatty acids obtained by way of lipolysis. Customary soap additives are fatty acids, fatty alcohols, lanolin, lecithin, vegetable oils, partial glycerides, inter alia, fat-like substances for lipid replenishment of the cleansed skin, antioxidants such as ascorbil palmitate or tocopherol for preventing auto-oxidation of the soap (rancidity), complexing agents such as nitrilotriacetate for binding heavy metal traces that could catalyze the auto-oxidative spoilage, perfume oils for achieving the desired fragrance notes, dyes for coloring the bars of soap, and optionally specific additives.

Liquid soaps are based on both K salts of natural fatty acids and on synthetic anionic surfactants. In aqueous solution, they contain fewer substances that provide washing action than solid soaps, and include the customary additives, optionally including viscosity-regulating components, and pearlescence additives. Due to the convenient and hygienic application from dispensers, they are used in public lavatories and the like. Washing lotions for particularly sensitive skin, based on mild synthetic surfactants comprising additives of skin care substances, are set to a neutral or slightly acidic pH (pH 5.5).

For cleansing primarily facial skin, a number of additional preparations are available, such as facial toners, cleansing lotions, cleansing milks, cleansing creams and cleansing pastes; face packs are used in part for cleansing, but they generally refresh and nourish the facial skin. Facial toners are typically aqueous-alcoholic solutions having a low surfactant content and further skin care substances. Cleansing lotions, milks, creams and pastes are typically based on O/W emulsions that have a relatively low fatty component content and have cleansing and nourishing additives. Scruffing and peeling preparations contain substances that have a mild keratolytic effect to remove the uppermost necrotic layers of dead skin, in part comprising additives of abrasively acting powder. Almond bran, which has long been used as a mild skin cleansing agent, is frequently still a component of preparations of this kind today. Agents for the cleansing treatment of blemished skin also contain antibacterial and anti-inflammatory substances, since the accumulation of sebaceous material in comedones (blackheads) represents a breeding ground for bacterial infections and tends to cause inflammation. The wide range of different skin cleansing products offered varies in terms of the composition and content of different active ingredients depending on different skin type and specific treatment purposes.

Further cosmetic agents may include agents for influencing body odor. This refers in particular to deodorizing agents. Deodorants of this kind are able to mask, remove or destroy odors. Unpleasant body odors arise from the bacterial decomposition of sweat, in particular in the warm and moist axilla regions, where microorganisms encounter good living conditions. As a result, antimicrobial substances are the most important ingredients of deodorants. In particular, antimicrobial substances that have a substantially selective effectiveness with respect to the bacteria responsible for body odor are possible. Non-limiting active ingredients, however, have only a bacteriostatic effect and by no means completely destroy the bacterial flora. Antimicrobial agents include in general all suitable preservatives that specifically work against gram-positive bacteria. These are, for example, Irgasan DP 300 (trichloro, 2,4,4'-trichloro-2'-hydroxydiphenyl ether), chlorhexidine (1,1'-hexamethylenebis(5-(4'-chlorophenyl)-biguanide) and 3,4,4'-trichlorcarbanilide. Quaternary ammonium compounds are also suitable in principle. Because of their high antimicrobial effectiveness, all these substances are used only in low concentrations of about 0.1 to 0.3 wt. %. Furthermore, numerous odorants also have antimicrobial properties. Accordingly, such odorants having antimicrobial properties are used in deodorants. In particular, farnesol and phenoxyethanol should be mentioned in this regard. The deodorants may include bacteriostatically effective odorants. The odorants may be present again in the form of heterocycles. However, it is also possible that it is precisely these antibacterially effective odorants that are not used in the form of heterocycles and are then used in mixtures with other odorants which are present as heterocycles. A further group of essential ingredients of deodorants are enzyme inhibitors, which inhibit the enzymatic decomposition of sweat, such as triethyl citrate or zinc glycinate, for example. Essential ingredients of deodorants are furthermore also antioxidants, which are intended to prevent oxidation of sweat components.

In a further likewise embodiment, the cosmetic agent is a hair setting agent that contains polymers for setting. At least one polyurethane may be present among the polymers.

Finally, the composition also covers air care agents, for example in the form of sprays, and insect repellents, which in addition to the heterocycles described herein may contain the ingredients typical and known for such agents.

In principle, all embodiments disclosed in connection with the heterocycles and the agents of the composition are also applicable to the processes and uses described, and vice versa. For example, it is self evident that all specific heterocycles described herein are applicable to said agents and methods and can be used as described herein.

EXAMPLES

General Method
Production of Enamines

Imidazole (4.08 g, 60 mmol) was dissolved in anhydrous dichloromethane (DCM) (30 mL) followed by addition of thionyl chloride (1.09 mL, 15.0 mmol). The reaction mixture was stirred for 20 minutes at room temperature. The resulting precipitate was filtered and the filtrate was treated with thionyl chloride (1.09 mL, 15.0 mmol) and stirred at room temperature for 5 minutes followed by dropwise addition of the aldehyde or ketone (10 mmol). The mixture was stirred for one hour at room temperature. The progress of the reaction was monitored by means of thin layer chromatography (1% $NEt_3$ (v/v) in EtOH/DCM, 2:98). The reaction was quenched by dilution with 20 mL DCM and addition of saturated aqueous $NaHCO_3$ (20 mL) solution. The phases were separated and the organic phase was dried over $MgSO_4$ and then filtered. The solvent was removed in vacuo and the crude product was purified by column chromatography (EtOAc, EtOH or iso-PrOH, 1% (v/v) $NEt_3$) to give the desired compound as a mixture of isomers.

Example 1: Ketone=benzylacetone; 1-(1-phenethylthyl)-1H-imidazole (1) and 1-(1-methyl-3-phenyl-1-propenyl)-1H-imidazole (2)

The following compounds (mixture of diastereomers) were prepared by the general method described above.

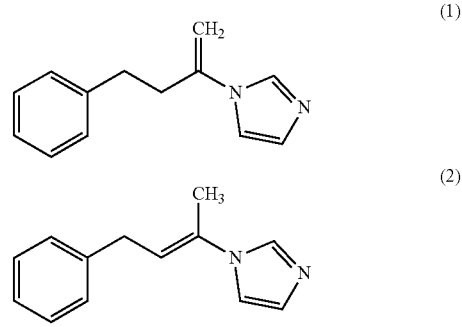

(1): Yellow Oil.

$R_f$ (1% $Et_3N$ (v/v) in EtOAc/EtOH, 7:3)=0.65.

$^1H$ NMR ($CDCl_3$) −7.70 (s, 1H), 7.38-7.26 (m, 2H), 7.26-7.19 (m, 1H), 7.18-7.09 (m, 4H), 5.08 (d, J=1.1 Hz, 1H), 4.78 (d, J=1.1 Hz, 1H), 2.87-2.76 (m, 4H). $^{13}C$ NMR ($CDCl_3$) −142.1, 140.2, 135.2, 130.1, 128.7 (2C), 128.5 (2C), 126.4, 117.1, 103.9, 35.9, 33.4.

MS (ESI, +ve) −199 $[M+H]^+$

IR (UATR): $\tilde{v}$ ($cm^{-1}$) −3110 (w), 3027 (w), 2929 (w), 1652 (s), 1488 (s), 1317 (m), 1247 (m), 1078 (m).

(2): Colorless Oil.

$R_f$ (1% $Et_3N$ (v/v) in EtOAc/EtOH, 7:3)=0.57.

$^1H$ NMR ($CDCl_3$) −7.68 (s, 1H), 7.37-7.29 (m, 2H), 7.29-7.16 (m, 3H), 7.11 (s, 1H), 7.07 (s, 1H), 5.78 (tq, J=7.7 Hz, J=1.2 Hz, 1H), 3.53 (d, J=7.7 Hz, 2H), 2.24 (d, J=1.1 Hz, 3H).

$^{13}C$ NMR ($CDCl_3$) −139.6, 135.1, 132.0, 129.6, 128.7 (2C), 128.5 (2C), 126.5, 118.7, 117.1, 35.5, 16.0.

MS (ESI, +ve) −199 $[M+H]^+$

IR (UATR): $\tilde{v}$ ($cm^{-1}$) −3110 (w), 3027 (w), 2923 (w), 1672 (m), 1490 (s), 103 (m), 1243 (m), 1069 (m).

Example 2: Ketone=methyl nonyl ketone; 1-(2-undec-1-enyl)-1H-imidazole (3) and 1-(2-undec-2-E,Z-enyl)-1H-imidazole (4)

The following compounds (mixture of isomers) were prepared by the general method described above.

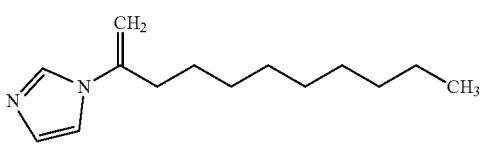

(3)

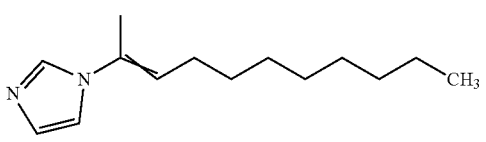

(4)

(3): Yellow Oil.
R$_f$ (1% Et$_3$N (v/v) in MTBE/$^i$PrOH, 7:3)=0.65.
$^1$H NMR (CDCl$_3$) −7.66 (s, 1H), 7.10 (s, 1H), 7.08 (s, 1H), 5.04 (s, 1H), 4.78 (s, 1H), 2.53-2.43 (m, 2H), 1.52-1.42 (m, 2H), 1.37-1.17 (m, 12H), 0.91-0.79 (m, 3H).
$^{13}$C NMR (CDCl$_3$) −143.0, 135.1, 129.7, 117.0, 102.7, 33.9, 31.8, 29.4, 29.2 (2C), 28.9 (2C), 22.6, 14.1.
MS (ESI, +ve) −221 [M+H]$^+$
IR (UATR): ṽ (cm$^{-1}$) −3112 (w), 2924 (s), 2854 (m), 1651 (m), 1487 (s), 1466 (m), 1376 (w), 1318 (m), 1246 (m), 1108 (m), 1073 (m), 1006 (m), 870 (m), 812 (m), 723 (s), 657 (s).
(4): Yellow Oil.
R$_f$ (1% Et$_3$N (v/v) in MTBE/$^i$PrOH, 7:3)=0.65.
$^1$H NMR (CDCl$_3$) −7.61 (s, 1H), 7.06 (s, 1H), 7.04 (s, 1H), 5.60-5.52 (m, 1H), 2.19-2.07 (m, 5H), 1.53-1.38 (m, 2H), 1.38-1.14 (m, 10H), 0.96-0.80 (m, 3H).
MS (ESI, +ve) −221 [M+H]$^+$ Example 3: Ketone=methyldihydrojasmonate; Methyl 3-(1H-imidazol-1-yl)-2-pentylcyclopent-3-enoacetate (5)

The following compound was prepared by the general method described above.

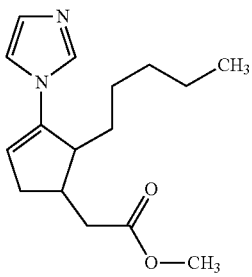

(5)

(3): Yellow Oil.
R$_f$ (1% Et$_3$N (v/v) in EtOAc/EtOH, 7:3)=0.70.
$^1$H NMR (CDCl$_3$) −7.59 (s, 1H), 7.04 (s, 1H), 7.01 (s, 1H), 5.55 (s, 1H), 3.63 (s, 3H), 2.81-2.05 (m, 6H), 1.59-1.02 (m, 8H), 0.92-0.68 (m, 3H).
$^{13}$C NMR (CDCl$_3$) −172.9, 139.3, 135.2, 129.6, 117.2, 113.1, 51.5, 50.0, 40.7, 38.0, 35.2, 31.9, 31.8, 26.2, 22.4, 13.9.
MS (ESI, +ve) −277 [M+H]$^+$
IR (UATR): ṽ (cm$^{-1}$) −3114 (w), 2918 (m), 2850 (m), 1734 (s), 1656 (w), 1490 (m), 1463 (m), 1370 (w), 1292 (m), 1242 (m), 1197 (m), 1170 (m), 1107 (m), 1052 (m), 902 (m), 808 (m), 729 (s), 657 (s).

Example 4: Ketone=Nectaryl; 1-{2-[2-(4-Methylcyclohex-3-en-1-yl)propyl]cyclopent-1-en-1-yl}-1H-imidazole (6)

The following compound (isomeric mixture 1:1:1:1) was prepared by the general method described above.

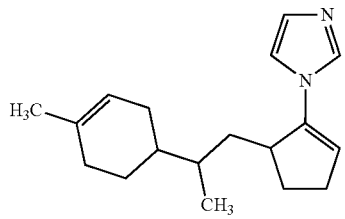

(6)

(3): Yellow Oil.
MS (ESI, +ve) −271 [M+H]$^+$

Example 5: Odor Test for Enamines of Benzylacetone

Used Compounds:

| Compound | Mass/mL | Concentration |
|---|---|---|
| 4-phenyl-2-butanone (benzylacetone; BA) MW = 148.40 g mol$^{-1}$, ρ = 0.989 g mL$^{-1}$ [2550-26-7] Alfa Aesar | 30.3 mg (EtOH) | 204.5 |
| Enamine Compounds (1)/(2) (63:37)$^a$ MW = 198.526 g mol$^{-1}$ | 40.4 mg | 203.8 |
| Phosphate buffer, pH 3.0 Prod. No.: 03082.3000 Bernd Kraft | | |

$^a$= determined by NMR

Method

The values given are mean values of two test persons. The samples were prepared as 200 mM solutions either in EtOH. The solution was absorbed on odor test strips. After the strips were soaked in the solution, they were dried for 30 minutes, then sprayed with pH 3.0 buffer and smelled after the following periods:
A—after 10 min (dry)
B—immediately after spraying with buffer
C—18 hours after spraying
D—24 hours after spraying
E—48 hours after spraying
F—72 hours after spraying
G—6 days after spraying The controls were not sprayed with buffer but sniffed at without previous spraying after the specified time. "Activated" means that the corresponding sample was sprayed with buffer. The odor intensity is rated on a scale of 0 (no odor) to 6 (very strong). The results are shown in Table 1.

TABLE 1

| 200 mM in EtOH | A | B | C | D | E | F | G |
|---|---|---|---|---|---|---|---|
| BA (control) | 5.0 | 5.0 | 1.50 | 1.0 | 1.0 | 0.75 | 0.75 |
| BA-Enamine (control) | 3.0 | 3.0 | 3.75 | 3.0 | 3.0 | 2.5 | 2.5 |
| BA enamine (activated) | 3.0 | 4.25 | 3.25 | 2.0 | 2.5 | 2.75 | 2.0 |

Example 6: Smell Test for Enamines of Methyl Nonyl Ketone and Nectaryl

Used Compounds:

| Compound | Mass/mL | Concentration |
| --- | --- | --- |
| 2-undecanone (methylnonyl ketone, MNK) MW = 170.29 g mol$^{-1}$, ρ = 0.8259 g mL$^{-1}$ [112-12-9] Sigma Aldrich | 34.4 mg | 202.0 |
| Enamine compound (3) MW = 220.35 g mol$^{-1}$ | 47.7 mg | 216.5 |
| 2-(2-[4-methyl-3-cyclohexen-1-yl]propyl)cyclopentanone (Nectaryl) MW = 220.35 g mol$^{-1}$ ρ = 0.964 g ml$^{-1}$ [95962-14-4] Givaudan | 45.5 mg | 206.5 |
| Enamine compound (6) MW = 270.41 g mol$^{-1}$ Phosphate buffer, pH 3.0 Prod. No.: 03082.3000 Bernd Kraft | 56.6 mg | 209.3 |

The results were evaluated as indicated in Example 5 and are shown in Table 2.

TABLE 2

| | A | B | C | D | G |
| --- | --- | --- | --- | --- | --- |
| 200 mM in EtOH (Control) | | | | | |
| MNK | 4.75 | 4.75 | 0.25 | 0.25 | 0.0 |
| MNK-enamine | 4.25 | 4.25 | 4.0 | 4.5 | 4.0 |
| Nectaryl | 4.25 | 4.25 | n.d. | 4.25 | 3.75 |
| Nectaryl enamine | 5.0 | 5.0 | n.d. | 5.0 | 4.0 |
| 200 mM in EtOH (activated) | | | | | |
| MNK | 4.75 | 5.0 | 0.25 | 0.0 | 0.0 |
| MNK-enamine | 4.25 | 5.0 | 3.75 | 3.75 | 3.5 | n.d. = not determined

Example 7: Boost for Enamines of Benzylacetone and Nectaryl

The compounds were also tested for their "odor boosting effect."

| Compound | Mass/mL | Concentration |
| --- | --- | --- |
| 2-undecanone (methylnonyl ketone, MNK) MW = 170.29 g mol$^{-1}$, ρ = 0.8259 g mL$^{-1}$ [112-12-9] Sigma Aldrich | 34.4 mg | 202.0 |
| Enamine compound (3) MW = 220.35 g mol$^{-1}$ | 47.7 mg | 216.5 |
| 2-(2-[4-methyl-3-cyclohexen-1-yl]propyl)cyclopentanone (Nectaryl) MW = 220.35 g mol$^{-1}$ ρ = 0.964 g mL$^{-1}$ [95962-14-4] Givaudan | 45.5 mg | 206.5 |
| Enamine compound (6) MW = 270.41 g mol$^{-1}$ Phosphate buffer, pH 3.0 Prod. No.: 03082.3000 Bernd Kraft | 56.6 mg | 209.3 |

The compounds were split into 2 batches:
Control (not sprayed with buffer) after 1, 4 and 5 days
Boost24 (after 24 h drying in the fume hood sprayed with buffer)
The results were evaluated as indicated in Example 5 and the results are shown in Table 3.

TABLE 3

| Condition | K | K (1 d) | K (6 d) | B24 (1 d) | B24 (5 d) |
| --- | --- | --- | --- | --- | --- |
| Day # | 0 | 1 | 2 | 2 | 6 |
| | A | B | E | F | I |
| EtOH MNK | 5.0 | 0.75 | 0.0 | 3.5 | 0.0 |
| MNK-enamine | 4.0 | 4.5 | 4.0 | 4.25 | 3.5 |
| EtOH Nectaryl | 4.0 | 4.5 | 2.5 | 4.0 | 3.0 |
| Nectaryl enamine | 5.0 | 4.5 | 4.0 | 4.5 | 4.0 |

K = control
B24 = Boost24

The invention claimed is:

1. A composition comprising:
an agent selected from the group consisting of a washing agent, a cleaning agent, a cosmetic agent, an air care agent, an insect repellent, or combinations thereof;
a surfactant; and
one or more heterocycles of the formula:

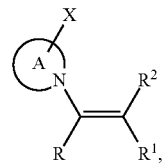

wherein:
R, R$^1$ and R$^2$ are independently selected from H, straight-chain or branched, saturated or unsaturated, substituted or unsubstituted hydrocarbon groups having from 1 to 20 carbon atoms and optionally up to 6 heteroatoms selected from 0, S, and N; or
R and R$^1$ or R and R$^2$ are combined with each other in order to form a cyclic group selected from substituted or unsubstituted aryl having up to 20 carbon atoms, substituted or unsubstituted heteroaryl having up to 20 carbon atoms and 1 to 6 heteroatoms selected from O, S, and N, substituted or unsubstituted cycloalkyl or cycloalkenyl having up to 20 carbon atoms, and substituted or unsubstituted heterocycloalkyl or heterocycloalkenyl having up to 20 carbon atoms and 1 to 6 heteroatoms selected from O, S, and N;
at least one of R, R$^1$, and R$^2$ is not H and the group —O—CR═CR$^1$R$^2$ is derived from an odoriferous ketone or odoriferous aldehyde of formula R—C(O)—CHR$^1$R$^2$;
wherein the odoriferous ketone or odoriferous aldehyde of formula R—C(O)—CHR$^1$R$^2$ is selected from the group of the following odoriferous ketones and aldehydes:

2-(2-[4-methyl-3-cyclohexen-1-yl]propyl)cyclopentanone, 2,6,10-trimethyl-9-undecenal, 3-(4-isopropylphenyl)-2-methylpropanal, 3-(3-isopropylphenyl)butanal, 3-(3,4-methylenedioxyphenyl)-2-methylpropanal, hydroxycitronellal, lauraldehyde, 3- and 4-(4-hydroxy-4-methylpentyl)-3-cyclohexene-1-carboxaldehyde, methylnonylacetaldehyde, 3-(4-tert-butylphenyl)-2-methylpropanal, phenylacetaldehyde, undecylenaldehyde, 2,6,10-trimethyl-9-undecenal, 3-dodecen-1-al, 2,6-dimethyl-5-heptenal, 2,4-dimethyl-3-cyclohexene-1-carboxaldehyde, 3-(4-tert-butylphenyl)-propanal, 2-methyl-3-(para-methoxyphenyl)propanal, 2-methyl-4-(2,6,6-trimethyl-2(1)-cyclohexen-1-yl)butanal, cis-/trans-3,7-dimethyl-2,6-octadien-1-al, 3,7-dimethyl-6-octen-1-al, [(3,7-dimethyl-6-octenyl)oxy]acetaldehyde, 1,2,3,4,5,6,7,8-octahydro-8,8-dimethyl-2-naphthaldehyde, 2,4-dimethyl-3-cyclohexene-1-carboxaldehyde, 2-methyl-3-(isopropylphenyl)propanal, 1-decanal, 2,6-dimethyl-5-heptenal, 4-(tricyclo[5.2.1.0(2,6)]-decylidene-8)-butanal, octahydro-4,7-methano-1H-indenecarboxaldehyde, alpha-methyl-3,4-(methylenedioxy)-hydrocinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexencarboxaldehyde, 1-dodecanal, 2,4-dimethylcyclohexene-3-carboxaldehyde, 4-(4-hydroxy-4-methylpentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-methoxyhexahydro-4,7-methanindane-1- or -2-carboxaldehyde, 3,7-dimethyloctan-1-al, 1-undecanal, 10-undecen-1-al, 1-methyl-3-(4-methylpentyl)-3-cyclohexencarboxaldehyde, 7-hydroxy-3,7-dimethyl-octanal, trans-4-decenal, 2,6-nonadienal, para-tolylacetaldehyde, 4-methylphenylacetaldehyde, 2-methyl-4-(2,6,6-trimethyl-1-cyclohexen-1-yl)-2-butenal, 3,5,6-trimethyl-3-cyclohexencarboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanindane-1-carboxaldehyde, 2-methyloctanal, alpha-methyl-4-(1-methylethyl)benzeneacetaldehyde, 6,6-dimethyl-2-norpinene-2-propionaldehyde, para-methylphenoxyacetaldehyde, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonylacetaldehyde, hexanal, trans-2-hexenal, 2-undecanon (methylnonylketone), methyl-beta-naphthylketone, musk indanone (1,2,3,5,6,7-hexahydro-1,1,2,3,3-pentamethyl-4H-inden-4-one), 6-acetyl-1,1,2,4,4,7-hexamethyltetraline, alpha-damascone, beta-damascone, delta-damascone, iso-damascone, damascenone, methyldihydrojasmonate, menthone, carvone, camphor, 3,4,5,6,6-pentamethylhept-3-en-2-one, fenchone, alpha-ionone, beta-ionone, gamma-methyl-ionone, 2-heptylcyclopentanone, dihydrojasmone, cis-jasmone, 1-(1,2,3,4,5,6,7,8-octahydro-2,3,8,8-tetramethyl-2-naphthalenyl)-ethan-1-one and isomers thereof, Methylcedrenylketone, acetophenone, methylacetophenone, para-methoxyacetophenone, methyl-beta-naphthylketone, benzylacetone, para-hydroxyphenylbutanone, celery ketone (3-methyl-5-propyl-2-cyclohexenone), 6-isopropyldeca-hydro-2-naphtone, dimethyloctenone, Frescomenthe (2-butan-2-ylcyclohexan-1-one), 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)indanone, 4-damascol, 4-(1,3-benzodioxol-5-yl)butan-2-one, 1-(2,6,6-trimethyl-2-cyclohexene-1-yl)-1,6-heptadien-3-one, isocyclemone E (2-acetonaphthon-1,2,3,4,5,6,7,8-octahydro-2,3,8,8-tetramethyl), methylnonylketone, methylcyclocitrone (1-(3,5,6-trimethyl-1-cyclohex-3-enyl)ethanone), methyl lavender ketone (3-hydroxymethylnonan-2-one), orivone (4-tert-amylcyclohexanone), 4-tert-butyl cyclohexanon, 2-pentyl cyclopentanone, 3-Methylcyclopentadecanone, 1-(5,5-dimethyl-1-cyclo-hexenyl)pent-4-en-1-one, Octahydro-7-methyl-1,4-methanonaphthalen-6(2H)-one, 2,2,5-trimethyl-5-pentylcyclopentan-1-one, 2,4,4,7-tetramethyl-oct-6-en-3-one, and 6,10-dimethylundecen-2-one; and A is selected from the group of substituted or unsubstituted compounds consisting of pyrazole, imidazole, benzimidazole, imidazoline, indole, quinoline, isoquinoline, purine, pyrimidine, oxazole, thiazole, 1,4-thiazine, xanthine, triazole, and tetrazole, and binds via this nitrogen atom to the rest of the molecule, wherein in A further carbon atoms may be replaced with N, O, or S, and at least one hydrogen atom of A may be substituted with a substituent X, wherein X is selected from —F, —Cl, —Br, —NO$_2$, —OH, =O, —CH$_3$, —CH$_2$CH$_3$.

2. The composition according to claim 1, wherein the agent is
(a) a liquid or gel-like agent;
(b) a powdery or granular agent;
(c) an agent in the form of shaped bodies;
(d) a cosmetic hair or skin treatment agent; or
(e) combinations thereof.

3. The composition according to claim 1, wherein the agent is a washing agent, cleaning agent, cosmetic agent, air care agent, or combinations thereof, and wherein the one or more heterocycles are present in an amount ranging from 0.001 to 5 wt. %;
wherein the agent is an insect repellant and the one or more heterocycles are present in an amount ranging from 0.001 to 100%;
or combinations thereof.

4. The composition according to claim 1, wherein R is a straight-chain or branched, saturated or unsaturated, substituted or unsubstituted hydrocarbon group having 1 to 20 carbon atoms and optionally up to 6 heteroatoms.

5. The composition according to claim 1, wherein:
(a) $R^1$ or $R^2$ is H and the other group is a straight-chain or branched, saturated or unsaturated, substituted or unsubstituted hydrocarbon group having from 1 to 20 carbon and optionally up to 6 heteroatoms; or
(b) $R^1$ and $R^2$ are H.

6. The composition according to claim 1, wherein $R^1$ and $R^2$ are H and R is a linear, substituted, alkyl group having up to 12 carbon atoms.

7. The composition according to claim 1, wherein A is selected from the group of substituted or unsubstituted compounds consisting of pyrazole, imidazole, benzimidazole, imidazoline, indole, quinoline, isoquinoline, purine, pyrimidine, oxazole, thiazole, 1,4-thiazine, xanthine, triazole and tetrazole, wherein the at least one substituent is selected from —F, —Cl, —Br, —NO$_2$, —OH, or =O, —CH$_3$, —CH$_2$CH$_3$.

8. The composition according to claim 1, wherein R is a linear or branched, substituted or unsubstituted, alkyl, alkenyl, or alkynyl group having up to 20 carbon atoms.

9. The composition according to claim 1, wherein R is a methyl, ethyl, propyl, butyl, pentyl, hexyl, heptyl, octyl, nonyl, or decyl, and optionally substituted with an aryl group.

10. The composition according to claim 9, wherein R includes the aryl group substituted at the terminal carbon atom.

11. The composition according to claim 1, wherein A is a unsubstituted or substituted compound selected from the following group consisting of imidazole, imidazoline, and pyrimidine.

12. The composition according to claim 1, wherein the odoriferous ketone or odoriferous aldehyde of formula R—C(O)—CHR$^1$R$^2$ is not acetone or acetophenone.

* * * * *